US009642905B2

(12) United States Patent
Jacobs

(10) Patent No.: US 9,642,905 B2
(45) Date of Patent: May 9, 2017

(54) VACCINE TO PROTECT A RUMINANT AGAINST PNEUMONIA CAUSED BY MANNHEIMIA HAEMOLYTICA

(71) Applicant: Intervet Inc., Madison, NJ (US)

(72) Inventor: Antonius Arnoldus Christiaan Jacobs, Kessel (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/777,672

(22) PCT Filed: Mar. 17, 2014

(86) PCT No.: PCT/EP2014/055244
§ 371 (c)(1),
(2) Date: Sep. 16, 2015

(87) PCT Pub. No.: WO2014/147001
PCT Pub. Date: Sep. 25, 2014

(65) Prior Publication Data
US 2016/0287690 A1   Oct. 6, 2016

(30) Foreign Application Priority Data

Mar. 18, 2013   (EP) .................................. 13159665

(51) Int. Cl.
| | | |
|---|---|---|
| *A61K 39/102* | (2006.01) | |
| *A61K 39/155* | (2006.01) | |
| *A61K 39/00* | (2006.01) | |
| *C12N 7/00* | (2006.01) | |
| *A61K 39/265* | (2006.01) | |

(52) U.S. Cl.
CPC .......... *A61K 39/102* (2013.01); *A61K 39/155* (2013.01); *A61K 39/265* (2013.01); *A61K 2039/522* (2013.01); *A61K 2039/5254* (2013.01); *A61K 2039/543* (2013.01); *A61K 2039/544* (2013.01); *A61K 2039/552* (2013.01); *A61K 2039/70* (2013.01); *C12N 7/00* (2013.01); *C12N 2710/16734* (2013.01); *C12N 2760/18534* (2013.01); *C12N 2760/18634* (2013.01)

(58) Field of Classification Search
None
See application file for complete search history.

(56) References Cited

U.S. PATENT DOCUMENTS

| | | | |
|---|---|---|---|
| 4,132,775 A * | 1/1979 | Volenec ............... | A61K 39/265 424/229.1 |
| 5,256,415 A | 10/1993 | Corstvet et al. | |
| 8,183,026 B2 | 5/2012 | Lawrence et al. | |
| 2004/0074446 A1 | 4/2004 | Hawn et al. | |
| 2005/0106185 A1 | 5/2005 | Briggs et al. | |
| 2005/0208060 A1 | 9/2005 | Haensler | |
| 2010/0062017 A1 | 3/2010 | Luo | |
| 2010/0104594 A1 | 4/2010 | Campogarrido et al. | |
| 2011/0212132 A1 | 9/2011 | Campogarrido et al. | |
| 2015/0297704 A1 | 10/2015 | Jacobs | |
| 2016/0287690 A1 | 10/2016 | Jacobs | |

FOREIGN PATENT DOCUMENTS

| | | |
|---|---|---|
| EP | 650734 A1 | 5/1995 |
| EP | 0810283 A2 | 12/1997 |
| WO | WO0149263 A1 | 7/2001 |
| WO | WO2004006851 A2 | 1/2004 |
| WO | 2004017990 A1 | 3/2004 |
| WO | 2005003330 A2 | 1/2005 |
| WO | WO2005077409 A1 | 8/2005 |
| WO | 2006122586 A1 | 11/2006 |
| WO | 2008118902 A1 | 10/2008 |

OTHER PUBLICATIONS

Cravens Rober L. US 20110165090 A1. pp. 1-3, Jul. 2011.*
Confer, A.W. et al., Bovine pneumonic pasteurellosis: Immunity to Pasteurella haemolytica, JAVMA, Nov. 15, 1988, pp. 1308-1316, vol. 193, No. 10.
Frank, G.H. et al., Effect of intranasal exposure to leukotoxin-deficient Mannheimia haemolytics at the time of arrival at the feedyard on subsequent isolation of M haemolytica from nasal secretions of calves, AJVR, May 2003, pp. 580-585, vol. 64, No. 5.
Frank, G.H. et al., Effects of vaccination prior to transit and administration of florfenicol at time of arrival in a feedlot on the health of transported calves and detection of Mannheimia haemolytica in nasal secretions, AJVR, Feb. 2002, pp. 251-256, vol. 63, No. 2.
Jericho, K.W.F. and Langford, E.V., Aerosol vaccination of calves with Pasteurella haemolytica against experimental respiratory disease, Can. J. comp. Med., Jul. 1982, pp. 287-292, vol. 46.
Jericho, K.W.F., Histological changes in lungs of calves exposed to an aerosol of Pasteurella haemolytica, J. Comp. Path., 1989, pp. 87-99, vol. 101.
Xue, W. et al., Immunogenicity of a modified-live virus vaccine against bovine viral diarrhea virus types 1 and 2, infectious bovine rhinotracheitis virus, bovine parainfluenza-3 virus, and bovine respiratory syncytial virus when administered intranasally in young calves, Vaccine, vol. 28, No. 22 2010, pp. 3784-3792.
Allen et al, Changes in the Bacterial Flora of the Upper and Lower, Can J Vet Res, 1992;, pp. 177-183, vol. 56.
Confer, A.W. et al., Antibody responses of cattle to outer membrane proteins of Pasteurella multocida A:3, AJVR, Oct. 1996, pp. 1453-1457, vol. 57, No. 10, EP.
Dabo et al, Pasteurella multocida and bovine respiratory disease, Animal Health Research Reviews, 2008, pp. 129-150, 8(2).
Highlander et al, Inactivation of Pasteurella (Mannheimia) haemolytica Leukotoxin, Infection and Immunity, Jul. 2000, p. 3916-3922, vol. 68, No. 7.

(Continued)

*Primary Examiner* — S. Devi

(57) ABSTRACT

The present invention pertains to a vaccine for administration to the upper respiratory tract of a ruminant to protect said ruminant against pneumonia caused by *Mannheimia haemolytica*, the vaccine comprising in combination live attenuated *Mannheimia haemolytica* bacteria, live attenuated parainfluenza-3 virus and live attenuated bovine respiratory syncytial virus, wherein the vaccine is for administration to the upper respiratory tract of the ruminant via intranasal atomization of the vaccine.

12 Claims, No Drawings

(56) References Cited

OTHER PUBLICATIONS

Hodgson, J.C., Efficacy of vaccination of calves against hemorrhagic septicemia with a live aroA derivative of Pasteurella multocida B:2 by two different routes of administration, Infection and Immunity, Mar. 1, 2005, pp. 1475-1481, vol. 73, No. 3.
International Search Report PCT/EP2014/055244 mailed on Apr. 28, 2014, 12 pages.
Kirkpatrick, J.G. et al., Effect of age at the time of vaccination on antibody titers and feedlot performance in beef calves, JAVMA, Jul. 1, 2008, pp. 136-142, vol. 233, No. 1, EP.
Kisiela et al;, Identification of Mannheimia haemolytica Adhesins Involved in, Infection and Immunity, Jan. 2009, p. 446-455, vol. 77, No. 1.
Panciera, R.J. et al., Bovine pneumonic pasteurellosis: effect of vaccination with live *Pasteurella* species, American Journal of veterinary research, Dec. 1984, pp. 2538-2542, vol. 45, issue 12.

\* cited by examiner

VACCINE TO PROTECT A RUMINANT AGAINST PNEUMONIA CAUSED BY MANNHEIMIA HAEMOLYTICA

CROSS-REFERENCE TO RELATED APPLICATIONS

This application is a national stage entry under 35 U.S.C. §371 of PCT/EP2014/055244, filed on Mar. 17, 2014, which claims priority under EP13159665.2, filed on Mar. 18, 2013, the contents of both of which are hereby incorporated by reference in their entireties.

The present invention pertains to a vaccine to protect a ruminant against pneumonia caused by *Mannheimia haemolytica* bacteria. The invention also pertains to the manufacture of such a vaccine and a method for protecting a bovine against pneumonia caused by *Mannheimia haemolytica* bacteria.

*Mannheimia haemolytica*, in particular serotype A1, is a commensal organism of the upper respiratory tract in ruminants, in particular bovine, and is the principal bacterial pathogen associated with pneumonic pasteurellosis (which is a commonly used term for indicating pneumonia induced by *Mannheimia haemolytica*) which leads to lung lesions. This is a severe form of disease that develops in the complex of bovine respiratory diseases (Dagmara Kisiela et al. in Infect. Immun. 2009 January; 77(1): 446-455). The bacteria commonly colonize the upper respiratory tract (including the nasal cavity, pharynx and larynx) without causing any physiological reaction such as disease or an immune response against these bacteria. Induction of disease is often associated with stress, especially from transportation, or infection with pathogenic viruses. Some protection against the disease may take place by vaccination of animals with a vaccine comprising live or killed *Mannheimia haemolytica* bacteria (also referred to as "MH" bacteria) as commonly known in the art. However in trials, independent of the type of vaccine (live or inactivated) and the route of administration (subcutaneous, intradermal, intramuscular or intranasal), the results of vaccination have been variable. Since 30 or more years, different studies and review articles have been published that describe all kinds of vaccines and administration routes to try and induce protection against challenge with wild type *Mannheimia haemolytica*.

In a review article Confer et al. (JAVMA, Vol. 193, No. 10, Nov. 15, 1988) report that ruminants vaccinated with live *Mannheimia haemolytica* by aerosol, ID (interdermal) or SC (subcutaneous) routes in some studies afforded a significant ($p<0.05$) lung lesion reduction after transthoracic challenge but in one study vaccination with live bacteria by the aerosol route failed to induce any protection. This is in line with Jericho et al. (Can. J. Comp. Med., 46:287-292, July 1982), who reports another study that shows that aerosol vaccination with live *Mannheimia haemolytica* will not provide adequate protection. The same way, Confer (supra) reports that many commercially available bacterin vaccines induce only insignificant reduction in number of lesions. He also states that an oil-type adjuvant improves protection. His conclusion is that to elicit maximal resistance against pneumonia most likely a combination of leukotoxin and bacterial surface components is necessary. In U.S. Pat. No. 5,256,415 it is shown that live attenuated *Mannheimia* bacteria when administered via subcutaneous implant produce satisfactory humoral response. Actual protection was present even when a known potentiator of bovine pasteurellosis (bovine viral diarrhoea virus), was present. However, when given by the aerosol route no more than an immune response is reported.

From Frank et al. (AJVR, Vol. 63, No. 2, February 2002), it is known that such a response after intranasal vaccination with a live attenuated strain may occur without having any protective effect. However, Frank et al. in an additional study (AJVR, Vol. 64, No. 5, May 2003) see some protection-related effect after intranasal vaccination with live attenuated *Mannheimia haemolytica* bacteria: the vaccination decreased the amount of colonization by wild-type *Mannheimia haemolytica*. No reduction in lung lesions however was reported.

It thus appears to be difficult to obtain actual protection against *Mannheimia haemolytica* (that is, actual reduction in lung lesion consolidation) which may be due to the fact that the disease, pasteurellosis, is a multifactorial disease.

The object of the invention is therefor to provide a vaccine that protects a ruminant against pneumonic pasteurellosis caused by *Mannheimia haemolytica*, which vaccine is safe in young animals (younger than 3-4 weeks of age). Protection against pneumonia in this sense is an actual statistically significant reduction in lung lesion scores ($p<0.05$; preferably $p<0.01$). It is preferred that in addition a significant reduction in pleuritis ($p<0.05$; preferably $p<0.01$) is provided, and further preferably a significant reduction of bacterial load in the lungs ($p<0.05$; preferably $p<0.01$) after challenge with pathogenic *Mannheimia haemolytica* bacteria.

To this end a vaccine has been devised comprising in combination live attenuated *Mannheimia haemolytica* bacteria, live attenuated parainfluenza-3 virus and live attenuated bovine respiratory syncytial virus, wherein the vaccine is for administration to the upper respiratory tract of the ruminant via atomisation of the vaccine. That is, the vaccine is administered by spraying it as a mist of fine particles heaving a volume averaged mean diameter of less than 200 μm, to reach at the upper respiratory tract of the ruminant. The administration of the attenuated *Mannheimia haemolytica* bacteria to the upper respiratory tract was expected to be inherently safe since even wild-type bacteria generally do not induce disease when present in the upper respiratory tract. However, it was not expected beforehand that an immune response, let alone adequate protection would be provided against wild-type *Mannheimia haemolytica* bacteria by administering the attenuated bacteria to the upper respiratory tract: even wild-type bacteria when present in this part of the respiratory tract do not induce an immune response under normal circumstances. Surprisingly, by administering the live attenuated *Mannheimia haemolytica* bacteria to the upper respiratory tract via atomisation in the presence of live attenuated parainfluenza-3 virus and live attenuated bovine respiratory syncytial virus, an adequate immune response against the *Mannheimia haemolytica* bacteria is induced, which response is suitable to obtain actual protection against a challenge with wild type bacteria. The reason for this is not 100% clear but may be related to a dual synergistic effect of having a huge mucosal area where the vaccine is delivered to the mucosa in combination with the presence of viruses that trigger an immune response in these mucosal surfaces. Although these viruses are attenuated and thus do not induce actual disease, viz. pathological effects in the mucosa of the respiratory tract, the immune response they do raise, in combination with the spreading of the vaccine via atomisation appears to be decisive in the ability of the novel vaccine for inducing an actual protective immune response against the *Mannheimia* bacteria present in the vaccine.

Many attenuated strains of *Mannheimia haemolytica* bacteria as such are known in the art (see e.g. Infection and Immunity, Vol. 86, No. 7, July 2000, p. 3916-3922; U.S. Pat. No. 8,183,026; US 2010/0104594 and US 2011/0212132). The type of attenuation is not important for the invention as such. The invention namely pertains to the surprising finding that an immune response against live attenuated *Mannheimia haemolytica* bacteria that provides protection against wild-type *Mannheimia haemolytica* bacteria, can be elicited even if these bacteria are administered to the upper respiratory tract (where wild-type *Mannheimia haemolytica* is present as a commensal and does not induce an immune response at all), when the administration takes place via atomisation in the presence of the viruses indicated above. It is understood that the type of attenuation of the *Mannheimia haemolytica* bacteria may affect the remaining virulence of the bacterium and therefore the safety and efficacy of the vaccine. However, balancing safety and efficacy to find the desired attenuation does not relate to the above mentioned finding of the present invention. The same way the particular strain or type of attenuation of the virus strains is not essential for the present invention: given the fact that the viruses are (inherently) totally unrelated to the bacterium, the specific immune response against the viruses simply cannot be essential for obtaining protection against the bacterium. It seems that the mere fact that a (mucosal) immune response is induced over a large mucosal surface is important for the present invention. Many attenuated live parainfluenza-3 viruses and live bovine respiratory syncytial viruses that evoke an immune response after administration to the upper respiratory tract are known in the art, such as for example from the commercially obtainable vaccines Inforce™ 3 (Pfizer Animal health), Nasalgen IP (Merck Animal Health), TSV-2™ (Pfizer Animal Health) and ONSET 5™ (Merck Animal Health).

It is noted that atomisation can be performed not only when the vaccine is in a liquid form (the particles then being droplets), but also when the vaccine is in a solid form (e.g. a lyophilized powder or cake of the strains in a stabiliser), in which case the vaccine may be spread as a fine powder, typically a powdered freeze-dried cake of the bacterium in a stabiliser matrix. It is estimated that a lower limit of the atomized particles (at least the volume averaged mean diameter) of 1 μm is practical, since to obtain smaller particles a high energy input may be needed which might be impractical.

The resulting vaccine is safe in young calves (less than 3-4 weeks of age), and protection against pneumonia caused by *Mannheimia haemolytica* bacteria, i.e. it evokes an immune response that provides a statistically significant reduction in lung lesion scores ($p<0.05$). In addition to this protection against pneumonia, the vaccine provides a significant reduction in pleuritis ($p<0.05$), and a significant reduction in bacterial load in the lungs ($p<0.05$) after challenge with pathogenic *Mannheimia haemolytica* bacteria.

Therefore, in a further embodiment, the vaccine according to the invention is for administration to bovines, preferably at an age of less than 4 weeks.

The invention also pertains to the use of live attenuated *Mannheimia haemolytica* bacteria and in combination therewith live attenuated parainfluenza-3 virus and live attenuated bovine respiratory syncytial virus, for the manufacture of a vaccine comprising both the bacteria and the viruses, which vaccine upon administration to the upper respiratory tract of a ruminant via atomisation provides protection against pneumonia caused by *Mannheimia haemolytica* bacteria; And to a method to protect a ruminant against pneumonia caused by *Mannheimia haemolytica* bacteria, the method comprising administering to the upper respiratory tract of said ruminant via atomisation a vaccine comprising in combination live attenuated *Mannheimia haemolytica* bacteria, live attenuated parainfluenza-3 virus and live attenuated bovine respiratory syncytial virus.

It is noted that Xue et al. in Vaccine 28 (2010) 3784-3792 describe a MH-BRSV-Pi3 combination vaccine for intranasal application. However, Xue uses this vaccine only to check protection against the corresponding viral pathogens. Apparently, in line with common general knowledge, actual protection against wild type *Mannheimia haemolytica* was not expected by Xue. Moreover, Xue does not show or even suggest administration of the vaccine via atomization.

Although administration to the upper respiratory tract could take place via for example the mouth of the animal (oral administration of a fine mist of particles to reach the pharynx and optionally the larynx), the vaccine preferably is for intranasal administration. Intranasal administration has proven to lead to a good mucosal immune response against the bacterium.

As is well known in the art, intranasal administration is defined as administration 'by way of the nasal structures' (Merriam-Webster online dictionary (m-w.com); or as: administration 'within the nose' (The American Heritage® Medical Dictionary, Houghton Mifflin Company).

In an embodiment the atomisation provides a mist of vaccine particles having an (volume) average particle size below 50 μm in diameter. It is recognised that by having smaller particles, a larger the surface of the mucosa that can be directly reached by the vaccine. This is believed to lead to an improved immune response. A particle size below 50 μm has proven to be practical and adequate for eliciting an immune response. In a further embodiment the average particle size is between 20 and 40 μm in diameter. In an embodiment the vaccine comprises live attenuated infectious bovine rhinotracheitis virus. This is believed to further increase the adequateness of the immune response against *Mannheimia haemolytica* since this virus, even when attenuated is known to trigger a mucosal immune response.

It is noted that the term "vaccine" in the sense of this invention is a constitution suitable for application to an animal, comprising one or more antigens in an immunologically effective amount (i.e. capable of stimulating the immune system of the target animal sufficiently to at least reduce the negative effects of a challenge of the wild-type micro-organisms), typically combined with a pharmaceutically acceptable carrier such as a liquid containing water, optionally comprising immunostimulating agents (adjuvants), which upon administration to the animal induces an immune response for treating a disease or disorder, i.e. aiding in preventing, ameliorating or curing the disease or disorder. In general, a vaccine can be manufactured by using art-known methods that basically comprise admixing the antigens (or a composition containing the antigens) with a pharmaceutically acceptable carrier, e.g. a liquid carrier such as (optionally buffered) water or a solid carrier such as commonly used to obtain freeze-dried vaccines. For a live vaccine an immunologically effective amount is typically between $10^4$-$10^9$ CFU/dose for bacteria and between $10^3$-$10^{10}$ TCID$_{50}$/dose for viruses, although depending on the attenuation the number may be lower (for less attenuated micro-organisms) or higher (for more attenuated micro-organisms). Optionally other substances such as adjuvants, stabilisers, viscosity modifiers or other components are added depending on the intended use or desired properties of the vaccine. For vaccination many forms are suitable, in particular liquid formulations (with dissolved, emulsified or suspended antigens; typical administration volumes are between 0.1 and 10 ml, preferably between 0.2 and 5 ml, preferably 2 ml or less) but also solid formulations such as powders for atomisation devices may be suitable.

In a further embodiment, the vaccine according to the invention is applied by a single administration, preferably the administered volume is divided over both nostrils.

The term attenuated as used herein refers to the incapability of a microorganism, in particular a bacterium or virus, of inducing a full suite of symptoms of the disease that is normally associated with its virulent (often wild-type) pathogenic counterpart. It may be attenuated such that it does not replicate within a host cell or animal, or replicate at a rate which is not significantly detrimental to the cell or animal, and/or does not induce a detrimental host response. An attenuated strain may exhibit a reduced ability to survive in a host, and may contain one or more mutations in one or more virulence genes as is commonly known in the art.

In an embodiment, the vaccine according to the invention comprising live attenuated *Mannheimia haemolytica* bacteria for protection of a ruminant against pneumonia caused by *Mannheimia haemolytica*, by administration of the vaccine to the upper respiratory tract of the ruminant via atomisation of the vaccine, is characterised in that the administration takes place via intranasal atomisation; the vaccine particles have an average particle size between 20 and 40 µm in diameter; the vaccine additionally comprises live attenuated parainfluenza-3 virus and live attenuated bovine respiratory syncytial virus, and optionally also comprises infectious bovine rhinotracheitis virus; the live attenuated *Mannheimia haemolytica* bacteria are from a streptomycin dependent strain.

The invention will further be explained based on the following examples.

EXAMPLE 1

Several atomization devices were assessed with respect to the obtained particle size. In this example, three cannulas were tested, which cannulas can be secured to standard syringes. The first cannula is the LMA MAD Nasal™ ("MAD"), available from LMA North America Inc., San Diego, Calif., USA. The second cannula is the Rispoval™ applicator ("Pfizer"), available from Pfizer Animal Health, Brussels, Belgium. The third cannula is a 1" blue flex applicator nozzle available from Genesis Industries, Inc. Elmwood, Wis., USA ("Genesis").

These cannulas were tested with regular WFI (water-for-injection) and the obtained volume averaged droplet size was established using a Sympatec™ particle size analyser. The results are indicated below in Table 1.

TABLE 1

Mean droplet size with various cannulas

| Cannula type | Volume average size (diameter in µm) | Standard deviation (µm) |
| --- | --- | --- |
| MAD | 32.8 | 8.8 |
| Pfizer | 39.5 | 4.6 |
| Genesis | 197 | Not determined |

It appears that with all three cannulas atomization of the WFI can be achieved. For the further experiments the MAD cannula was used.

EXAMPLE 2

The objective of this experiment was to test the efficacy of intranasal vaccination with an atomization device with a live MH-BRSV-Pi3 vaccine in 2-week-old calves against *Mannheimia haemolytica* M 7/2 challenge. The vaccine contains live *Mannheimia haemolytica* (ΔlktA), live BRSV (the "Jencine" strain; the same strain as in the product "Jencine 4", available from Merck Animal Health, Summit, N.J., USA)) and live Pi3 (the strain "INT2"; the same strain as in the product Bovilis® IBR-PI3 live, available from MSD Animal Health, Boxmeer, The Netherlands).

Experimental Design

Twenty clean catch and colostrum deprived calves (2-3 weeks of age at day of vaccination) were used for the experiment. Ten calves were vaccinated once intranasally with the live MH-BRSV-Pi3 vaccine and ten calves were left as unvaccinated control. Three weeks after vaccination all calves were challenged intratracheally with *Mannheimia haemolytica*. During 7 days after challenge, the calves were observed for the development of clinical signs of respiratory disease. At 7 days post-challenge (or earlier in case of severe clinical signs), the calves were killed and necropsied, and examined for lung lesions, pleuritis and bacterial load.

Vaccine

The vaccine was constituted based on the following compounds:
freeze dried *Mannheimia haemolytica* ΔlktA, strain D153, serotype A1, which does not produce active leukotoxin, in Rho BACF stabilizer.
frozen live BRSV strain Jencine, diluted to a titer of 5.7 $\log_{10}$ TCID$_{50}$/ml at day of vaccination and put on ice, and
frozen live Pi3 strain INT2, diluted to a titer of 5.7 $\log_{10}$ TCID$_{50}$/ml at day of vaccination and put on ice.

Right before vaccination, the freeze dried *Mannheimia haemolytica* cake was dissolved in Unisolve to aim at 1.5×10$^8$ CFU/ml. The three compounds were mixed in equal volumes. The vaccine was administered intranasally into both nostrils (1 ml per nostril) using the MAD atomisation device. The bacterial titre in the vaccine was verified immediately after use (life count). The titre was 8.4×10$^7$ CFU per 2 ml dose.

Challenge Culture

*Mannheimia haemolytica* M7/2 (serotype A1), was inoculated on bloodagar and incubated 16 hours at 37° C. Subsequently, one inoculation loop was inoculated in 100 ml TSB and incubated for 4-5 hours at 37° C. This culture was diluted, aiming at 2×10$^7$ CFU/ml. The actual titre of the challenge culture was verified by plate counting. The titre appeared to be 2.4×10$^7$ CFU per ml.

Vaccination

The calves were divided into two groups of 10 animals. Group 1 was vaccinated once intranasally with 2 ml (1 ml per nostril) using a syringe equipped with the MAD device. Group 2 was left as unvaccinated control. Vaccinates and controls were housed in separate rooms/compartments.

Challenge

Three weeks after vaccination all calves were challenged intratracheally with 30 ml challenge culture aiming at a challenge dose of approximately 6×10⁸ CFU per animal. The actual challenge dose was 7×10⁸ CFU.

Clinical Examination

After vaccination the calves were daily observed for any abnormalities of general health and/or behaviour.

Post-Mortem Examination

Seven days after challenge or earlier in case of severe clinical signs the calves were killed by electric sedation and subsequent bleeding to death, immediately followed by a post-mortem examination with special attention to the lungs. For each of the six lung lobes the % consolidation was estimated and recorded. The total lung score was obtained by addition of the % lung consolidations of the individual lung lobes (and thus theoretically is between 0 and 600). The lung consolidation is representative of pneumonia.

For each lung lobe fibrinous pleuritis was scored absent (0), mild (1), moderate (2) or severe (3) and recorded.

With regard to isolation of *M. haemolytica* from post-mortem samples, tissue samples were excised from eight standard sites representative of the lobes of each half of the lung (4 sites per half); diseased tissue was preferentially selected for each site, if it was present. The mirror image samples (the two samples of the equivalent lobe on each half) were pooled to give 4 samples per calf. Each pooled sample was submerged in boiling water for 3 seconds, homogenized, serially 10-fold diluted and inoculated (100 µl) on blood agar plates and then incubated for 16-24 hours at 37° C.

Statistical Analysis

The lung lesion scores (% consolidation) and pleuritis scores were evaluated by means of Generalized Estimating Equations (GEE, Agresti, 2002), taking into account the repeated measurement structure of the data. The percentage lung consolidation was converted into classes 0%=0, >0% to ≤5%=1, >5%≤10%=2 and then every 10% increase an increase of 1 unit. Re-isolation data were evaluated by the ANOVA for repeated measurements accounting for the correlation in the measurements of the lung parts in an animal.

All parameters were tested two-sided with the level of significance ($\alpha$) set at 0.05. Statistical analysis was carried out in the statistical programme SAS V9.1 (SAS Institute Inc. Cary N.C., USA).

Results

After vaccination (until challenge) all calves remained in good health and no vaccine related abnormalities were observed (data not shown). After challenge the control calves developed clear respiratory disease signs whereas the vaccinated calves developed much less signs. One control calf was found dead on day 2 after challenge and three control calves had to be euthanized on day 1 or 2 post-challenge because of severe clinical signs. None of the vaccinated calves died or had to be euthanized.

Post-mortem

Lung Consolidations

The lung consolidations in the vaccinates were significantly (74%) reduced compared to the controls: 40 versus 152 (p=0.0015, GEE). Of the 10 vaccinated animals, 7 had a lung consolidation lower than 30 (meaning less than about 5% consolidation per lobe), one had a score of 45 and two animals had a consolidation score of 125 and 175 respectively which resulted in the mean value of 40. Of the control animals, all had a score above 40 and seven had a score above 100.

Pleuritis

The pleuritis scores in the vaccinates were significantly (95%) reduced compared to the controls: 0.1 versus 2.0 (p=0.0040, GEE). In effect, hardly any pleuritis could be detected in the vaccinated animals. Even in the two vaccinated animals that had a consolidation score of 125 and 175 respectively, no pleuritis could be detected Bacterial Re-Isolation of *M. haemolytica* from Lungs The bacterial load in the vaccinates was significantly (about 5 $\log_{10}$) lower compared to that in the controls: 2.4 $\log_{10}$/ml versus 7.1 $\log_{10}$/ml (p=0.0001, ANOVA repeated measurements). This remarkable lowering of the bacterial load indeed corresponds to the significant effects seen with regard to lung consolidation and pleuritis.

The overall effect against the infection with *Mannheimia haemolytica* is believed to be markedly better than what is known from the prior art, since not only the lung consolidation is reduced by 74%, the pleuritis is virtually down to zero, and the bacterial load is down almost five orders.

The invention claimed is:

1. A method to protect a ruminant against pneumonia caused by *Mannheimia haemolytica* bacteria comprising administering a vaccine to the upper respiratory tract of the ruminant by intranasal atomisation of said vaccine, wherein said vaccine comprises live attenuated *Mannheimia haemolytica* bacteria, live attenuated parainfluenza-3 virus, and live attenuated bovine respiratory syncytial virus.

2. The method of claim 1, wherein the vaccine further comprises live attenuated infectious bovine rhinotracheitis virus.

3. The method of claim 1, wherein the atomisation provides a mist of vaccine particles having an average size below 50 µm in diameter.

4. The method of claim 3, wherein the average vaccine particle size is between 20 and 40 µm in diameter.

5. The method of claim 4, wherein the vaccine further comprises live attenuated infectious bovine rhinotracheitis virus.

6. The method of claim 3, wherein the vaccine further comprises live attenuated infectious bovine rhinotracheitis virus.

7. The method of claim 1, wherein the administration is to bovines at an age of less than 4 weeks.

8. The method of claim 1, wherein the vaccine is applied by a single administration.

9. The method of claim 8, wherein the volume of the single administration is divided over both nostrils.

10. The method of claim 3, wherein the administration is to bovines at an age of less than 4 weeks.

11. The method of claim 3, wherein the vaccine is applied by a single administration.

12. The method of claim 11, wherein the volume of the single administration is divided over both nostrils.

* * * * *